United States Patent
Johnsen et al.

[11] Patent Number: 6,036,490
[45] Date of Patent: Mar. 14, 2000

[54] DENTAL INSTRUMENT SERVICING SYSTEM

[75] Inventors: James B. Johnsen; Hal J. Oien, both of Beaverton, Oreg.

[73] Assignee: Jordco, Inc., Beaverton, Oreg.

[21] Appl. No.: 09/038,998

[22] Filed: Mar. 10, 1998

[51] Int. Cl.[7] .............................. A61C 5/02; A61G 15/00; A65C 3/00

[52] U.S. Cl. .............................. 433/102; 433/163; 433/77

[58] Field of Search .................................. 433/102, 163, 433/49, 75, 72, 77

[56] References Cited

U.S. PATENT DOCUMENTS

| | | | |
|---|---|---|---|
| 2,222,741 | 11/1940 | Bush | 32/1 |
| 2,539,940 | 1/1951 | Abramson | 224/28 |
| 2,665,479 | 1/1954 | Weldon | 433/163 |
| 3,107,832 | 10/1963 | Kotkins | 223/109.1 |
| 3,327,391 | 6/1967 | Malm | 433/163 |
| 3,473,991 | 10/1969 | Ludwig | 223/109 |
| 3,933,286 | 1/1976 | Karkas | 224/28 |
| 3,949,568 | 4/1976 | Gallagher | 61/1 A |
| 4,280,808 | 7/1981 | Johnsen et al. | 433/77 |
| 4,427,130 | 1/1984 | Szigeti | 221/4 |
| 4,643,674 | 2/1987 | Zdarsky | 433/102 |
| 4,717,057 | 1/1988 | Porteous | 224/217 |
| 4,726,470 | 2/1988 | Lieberman | 206/510 |
| 4,844,308 | 7/1989 | Porteous | |
| 4,901,847 | 2/1990 | Kesling | |
| 4,976,615 | 12/1990 | Kravitz | 433/75 |
| 5,016,795 | 5/1991 | Porteous | |
| 5,139,188 | 8/1992 | Scharf | |
| 5,368,482 | 11/1994 | Johnsen et al. | 433/163 |

FOREIGN PATENT DOCUMENTS

| | | | |
|---|---|---|---|
| 819512 | 10/1937 | France | 433/102 |
| 672565 | 2/1939 | Germany | 433/102 |

*Primary Examiner*—John J. Wilson
*Assistant Examiner*—Robyn K. Doan
*Attorney, Agent, or Firm*—Kolisch, Hartwell, Dickinson, McCormack & Heuser

[57] ABSTRACT

A finger-mounted dental instrument servicing system is provided, the system including a socket-forming member having a first end of predetermined contour, and a resiliently deformable cushion having a first end of a contour which mimics the contour of socket-forming member's first end. The cushion thus may be provided with a plurality of distinct surface regions, each surface region being configured to receive endodontic files or related instruments of a particular size or type. In this manner, the servicing system may be used both to service the files, and as a dental organizer. A finger mount is attached to the socket-forming member, accommodating use of the system by a wearer without the need for an additional pair of hands.

20 Claims, 1 Drawing Sheet

DENTAL INSTRUMENT SERVICING SYSTEM

TECHNICAL FIELD

The present invention relates generally to the field of dentistry, and, more particularly, to a finger-mounted system whereby the servicing and temporary storage of dental instruments may be achieved. Although useful in a variety of contexts, the system is believed to be especially well suited for use in the servicing and storage of endodontic files and of other dental instruments, and is described in that context below.

BACKGROUND ART

During conventional dental maintenance and treatment procedures, dentists and dental technicians are required to perform tasks using a variety of instruments which must be readily available to the dentist. In an endodontic procedure, for example, dentists must have ready access to endodontic files which gauge the depth of root canals prepared in the patient's teeth. A dental assistant thus typically is employed to hold a file dispenser from which the dentist can withdraw fresh endodontic files, and into which he/she can place used instruments.

It also will be understood that most dental instruments require periodic servicing, often during performance of a procedure such as the endodontic procedure described above. Endodontic files, for example, commonly are used with depth markers placed at preselected positions along the file's shaft. Similarly, both files and other dental instruments may require periodic cleaning, removal of debris, or application of a medicament or other preparation. Again, this commonly is achieved by making a dental assistant available, the assistant generally being given the tedious task of holding a gauze sponge on which the instruments may be wiped, or holding a container which carries the medicament or other preparation.

The aforementioned arrangement, however, represents a waste of valuable time, the efforts of two professionals being used where the efforts of a single professional would suffice. One alternative has been to simply place the gauze sponge and paste on a tray where they may be accessed by the dentist or technician without the aid of an assistant. Not surprisingly, this arrangement also leads to a waste of time, the dentist or technician being required to pick up the gauze sponge or preparation each time an instrument is to be serviced. Another alternative involves the use of finger-mounted prophylactic paste holder units, but such units generally are single-purpose appliances which do nothing more than hold a medicament or the like. Furthermore, there is a risk associated with this practice, namely, the dental assistant risks being pierced by a file, potentially resulting in serious infection.

Accordingly, one object of the present invention is to provide a more complete dental servicing system which may be mounted to a user's hand. More particularly, it is an object of the invention to provide a dental servicing system which may be worn without interfering with the wearer's ability to perform dental tasks. It is also an object of the invention to protect the wearer from possible injury due to contact with dental instruments, and to protect the instruments from possible contamination due to contact with the wearer.

SUMMARY OF THE INVENTION

The invented dental instrument servicing system is a finger-mounted system which includes a socket-forming member having a first end of predetermined contour, and a resiliently deformable cushion having a first end of a contour which mimics the contour of socket-forming members first end. The cushion thus may be provided with a plurality of distinct surface regions, each surface region being configured to receive endodontic files or other instruments of a particular size or type. In this manner, the servicing system may be used both to service the files, and as a dental organizer. A finger mount is attached to the socket-forming member, accommodating use of the system by a wearer without the need for an additional pair of hands.

In the depicted embodiment, the socket-forming member includes a pair of spaced walls, each having a first end of predetermined contour. The walls define a tapered socket, the system's cushion being tapered similarly for receipt within the socket such that the contour of the first edge of the cushion mimics the contour of the first edges of the walls. The cushion thus is isolated from the system finger mount, protecting the user from puncture injury or the like. A measuring platform also typically is provided, extending from the wall member, above the finger mount, so as to further protect the user. The measuring platform includes a scale for use in setting a depth marker on an endodontic file.

The system also may include a medicament holder configured for securement to the socket-forming member, the holder being fitted both with a clip which fastens to a socket-forming member wall. Additionally, a service platform may be provided, typically extending generally perpendicularly from the wall member and generally flush with the first end of the wall member. The service platform defines one or more recessed openings, each configured to receive a depth marker for application to an endodontic file.

These and other objects and advantages of the present invention will be more readily understood after a consideration of the drawings and the detailed description of the preferred embodiment which follows.

DETAILED DESCRIPTION OF THE PREFERRED EMBODIMENT AND BEST MODE FOR CARRYING OUT THE INVENTION

The present invention relates to a system which has been adapted for use in the servicing of dental instruments, and for the organizing of dental instruments such as endodontic files in a manner which is both safe and convenient.

The invention arises from improvements to apparatus which we previously developed, and from the adaptation of such apparatus to incorporate these improvements. The previously-developed apparatus are the subject of U.S. Pat. No. 4,280,808, entitled "Endodontic File Holder", and U.S. Pat. No. 5,368,482, entitled "Dental Instrument Servicing System", both of which are commonly owned herewith. The disclosures of these patents are incorporated herein by this reference.

Figure 1:
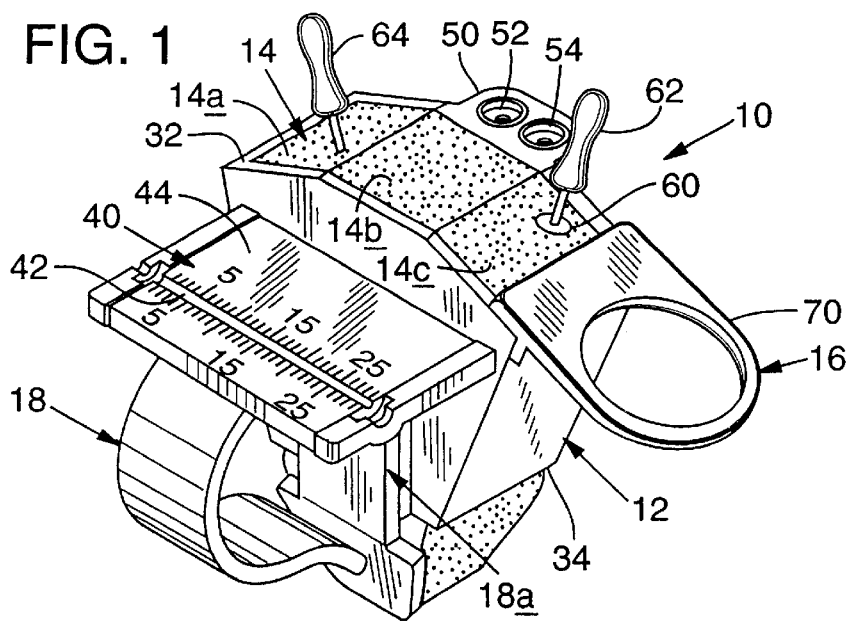
FIG. 1 is an isometric view of a dental instrument servicing system constructed in accordance with the present invention, the system including a socket-forming member, a cushion, a medicament holder, and a finger mount.

Referring initially to FIG. 1, the reader is provided with an isometric illustration of an exemplary servicing system, the system being indicated generally at 10. As shown, system 10 includes a socket-forming member 12, which in turn caries a cushion 14, a medicament holder 16, and a finger mount 18. Each of the aforementioned cushion, medicament holder and finger mount are selectively removable form the socket-forming member as will be described below.

Figure 2:
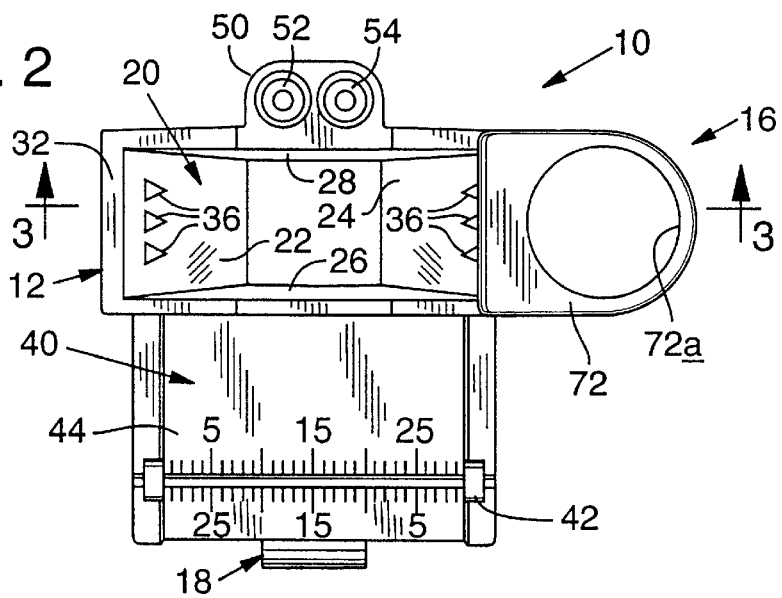
FIG. 2 is a top view of the dental instrument servicing system shown in FIG. 1, the system's cushion having been removed.
Figure 3:
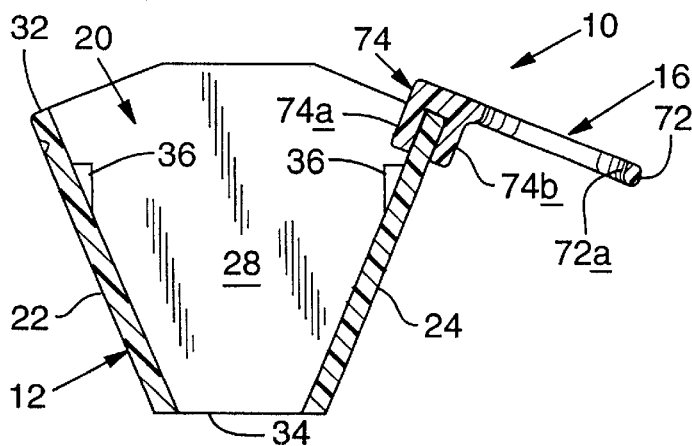
FIG. 3 is a sectional side view of the system shown in FIG. 2, the view being taken generally along line 3—3 of FIG. 2.

Focusing first on the details of socket-forming member 12, and referring for that purpose to FIGS. 1–3, it will be noted that the socket-forming member defines a double-open-ended socket 20 which provides a seat for cushion 14. Although not required, the socket-defining member preferably is of unitary construction, being formed of a lightweight material such as plastic or aluminum. These materials, it will be appreciated, are inexpensive, are formable by molding process, and are suitable for hand-worn use.

As indicated, the socket-forming member includes four, generally planar side walls 22, 24, 26, 28 which extend between a first, upper end 32 of the socket-forming member and a second, lower end 34 of the socket-forming member. The walls tend toward convergence at the socket-forming member's lower end so as to define a socket which will tightly fit deformable cushion 14. The system's side walls also may be formed with projections 36, providing frictional anchors which help to maintain the cushion within the socket.

In the depicted embodiment, walls 22 and 24 converge at an angle of about 40-degrees, and walls 26 and 28 converge at a much smaller angle of about 3-degrees. The socket thus is defined with an inverted, truncated, generally pyramidal shape, with the cross-sectional area of the socket decreasing continuously from its upper end to its lower end (as viewed in FIG. 3).

The upper end of the socket-forming member is of predetermined contour, typically defining a plurality of distinct regions, each of which accommodates a different servicing operation. Side walls 26 and 28, for example, include corresponding first ends which are contoured to define three distinct socket opening regions, each of which faces in a different angular direction. Cushion 14 is placed within the socket, a first end of the cushion being configured to mimic the contour of the first end of the socket-forming member so as to define a plurality of distinct cushion surface regions 14a, 14b, 14c.

The socket-forming member also includes an outwardly projecting shelf 40, the shelf extending from wall 26 so as to cover finger mount 18. The shelf thus serves to protect the user's finger from injury by sharp instruments such as endodontic files which are inserted into the cushion. Those skilled will appreciate that the shelf also serves as a measuring device for use in connection with endodontic files, the shelf being provided with a trough 42 for receipt of endodontic files. In the preferred embodiment, the shelf is provided with a stainless steal cover 44 which enhances durability of the shelf. A scale is etched into cover 44, accommodating accurate positioning of depth markers on the file. The use of such a measuring device is more filly described in the aforementioned U.S. Pat. No. 4,280,808 which has been incorporated herein by reference above A service platform 50 projects from wall 28, the service platform being adapted for receipt of depth markers such as that shown at 60. The depth markers are used in connection with endodontic files 62, 64. As indicated, the shelf defines a pair of recessed openings 52, 54, each of which is configured to hold one or more depth markers for application to endodontic files. A depth marker thus may be applied to a file by insertion of the file through an aperture formed in the recessed opening. The service platform extends generally perpendicularly from the wall and generally flush with the upper end of the wall member, providing for enhanced protection of the user.

Returning to a discussion of the system's cushion, and referring for that purpose specifically to FIG. 1, it will be noted that cushion 14 is formed of a resilient, sponge-like material suitable for use in holding plural files such as endodontic files 60, 62 at the upper end of the cushion. The cushion also may be used to provide a cleaning surface which may be used to wipe debris from other dental instruments, or to perform other dental instrument servicing operations which will be familiar to those skilled in the art.

In its preferred form, the cushion is generally pie-shaped, being adapted to conform closely to the shape of the socket when placed therein. In fact, the upper end of the cushion has a predetermined contour which mimics the contour of the upper end of the socket-forming member, providing a plurality of distinct cushion surface regions, each adapted to receive files of predetermined size and/or style. Each cushion surface region is at an intersecting angle relative to an adjacent cushion surface region, providing clear delineations between the cushion surface regions. The system thus may be used to organize endodontic files by placement thereof into predetermined cushion surface regions. In FIG. 1, for example, file 62 is placed in right-most region 14c, whereas file 64 is in left-most region 14a.

To assemble the system, the cushion is removably inserted into the socket's upper opening, the lowermost portion of the cushion being pulled through the lower opening of the socket. Because the cushion is somewhat abrasive, it provides excellent frictional adherence to the socket-forming member.

Medicament holder 16 also is removably applied to the socket-forming member, the medicament holder being formed with a cup section 72 and a generally U-shaped clip section 74. The cup section is configured to hold a medicament in a dosage container. FIGS. 1–3 show a medicament holder 16 with a cup section having a hole 72a which is configured to receive a dosage container of predetermined size and shape. Clip section 74 includes an internal span 74a which extends along an interior of the socket-forming member and an external span 74b which extends along an exterior of the socket-forming member, the internal and external spans collectively securing the medicament holder to the socket-forming member.

Figure 4:
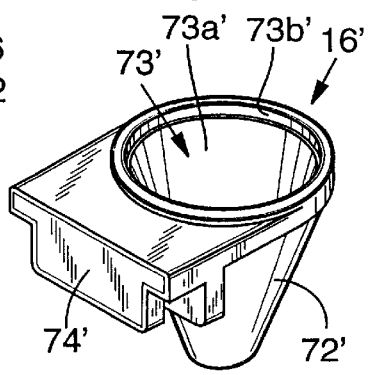
FIG. 4 is an isometric view of an alternative embodiment medicament holder.

FIG. 4 shows a medicament holder 16' with a cup section 72' which defines a cavity 73' for receipt of user-determined dosages of medicament. The cavity, it will be noted, includes a generally conical interior well section 73a' and a generally cylindrical interior well section 73b' adjacent the generally conical interior well section. As indicated, the generally conical interior well section is truncated to avoid waste of medicament which might otherwise be embedded (and unreachable) at the apex of the generally conical well section's interior. The holder also includes a clip section 74' which is similar to the clip section shown and described in FIGS. 1–3.

Referring once again to FIG. 1, it will be noted that finger mount 18 also is attached to socket-forming member 12, allowing for securement of the system to an individual's forefinger for use during a dental procedure. The finger mount preferably is removably attached to the socketforming member via a cooperative slide arrangement 18a, the specifics of which were described in our previously issued U.S. Pat. No. 4,280,808 which has been incorporated by reference herein. The system is suited for attachment to a user's finger, finger mount 18 encircling the user's forefinger and the next finger being used to stabilize the system from below (not shown). Because the system is relatively lightweight, it is not appreciatably more burdensome than a large ring, and does not significantly interfere with use of the wearer's hand. Those skilled in the art will appreciate that the depicted arrangement is representative only and that a variety of different finger-mounting arrangements may similarly be used.

While a preferred embodiment of the present invention has been shown and described with reference to the foregoing operational principles and preferred embodiment, it will be apparent to those skilled in the art that other changes in form and detail may be made without departing from the spirit and scope of the invention as defined in the appended claims.

We claim:

1. A dental instrument servicing system comprising:
    a socket-forming member including a pair of spaced wall members having corresponding first ends with upper surfaces of predetermined contour;
    a resiliently deformable cushion adapted for deformed seating within the socket-forming member, the cushion having a first end with an upper surface which mimics, and is flush with the the upper surfaces of the first ends of the socket-forming member walls to define a plurality of distinct cushion surface regions; and
    a finger mount joined with a preselected wall member of the socket-forming member to provide for attachment of said system to a use's hand.

2. The servicing system of claim 1, wherein the cushion is configured for placement within the socketforming member with the first end of the cushion within the socket-forming member.

3. The servicing system of claim 1, wherein the cushion is configured for placement within the socket-forming member with the first end of the cushion generally flush with the first ends of the wall members.

4. The servicing system of claim 1, wherein the first end of the cushion defines a plurality of generally planar cushion surface regions, each cushion surface region being at an intersecting angle with an adjacent cushion surface region.

5. The servicing system of claim 1 which further comprises a medicament holder configured for selected securement to the socket-forming member.

6. The servicing system of claim 5, wherein the medicament holder includes a clip having an internal span which extends along an interior of the socket-forming member and an external span which extends along an exterior of the socket-forming member, the internal and external spans collectively securing the medicament holder to the socket-forming member.

7. The servicing system of claim 5, wherein the medicament holder includes a generally U-shaped clip configured for removable attachment to an upper end of any wall of the socket-forming member.

8. The servicing system of claim 5, wherein the medicament holder includes a cup with a generally conical interior well section.

9. The servicing system of claim 8, wherein the generally conical interior well section is truncated.

10. The servicing system of claim 8, wherein the medicament holder cup further defines a generally cylindrical interior well section adjacent the generally conical interior well section.

11. The servicing system of claim 1 which further comprises a service platform which extends from the wall member opposite the finger mount.

12. The servicing system of claim 11, wherein the service platform extends generally perpendicularly from the wall member and generally flush with the first end of the wall member.

13. The servicing system of claim 11, wherein the service platform defines one or more recessed openings, each configured to receive a depth marker for application to an endodontic file.

14. The servicing system of claim 1 which further comprises a measuring platform which extends from the preselected wall member above the finger mount, the measuring platform including a scale for use in setting a depth marker on an endodontic file.

15. A system for use in servicing endodontic files, the system comprising:
    a socket-forming member including a pair of spaced wall members, each with an upper end having an upper surface of predetermined contour;
    a resiliently deformable cushion adapted for deformed seating within the socket-forming member, the cushion having an upper end with an upper surface which mimics, and is flush with the upper surfaces of the upper ends of the wall members to collectively define plurality of distinct, file-receiving regions in the cushion;
    a medicament holder configured for selected securement to the socket-forming member; and
    a finger mount joined with a preselected wall member of the socket-forming member to provide for attachment of said system to a user's hand.

16. The system of claim 15, wherein the medicament holder includes a generally U-shaped clip having an internal span which extends along an interior of the socket-forming member and an external span which extends along an exterior of the socket-forming member, the internal and external spans collectively securing the medicament holder to the socket-forming member.

17. The system of claim 16, wherein the medicament holder includes a cup with a generally conical interior well section and a generally cylindrical interior well section adjacent the generally conical interior well section.

18. The system of claim 15 which further comprises a service platform which extends generally perpendicularly from the wall member and generally flush with the upper end of the wall member, the service platform defining one or more recessed openings, each configured to receive a depth marker for application to an endodontic file.

19. The system of claim 15 which further comprises a measuring platform which extends from the preselected wall member above the finger mount, the measuring platform including a scale for use in setting a depth marker on an endodontic file.

20. A system for use in servicing endodontic files, the system comprising:
    a socket-forming member including a pair of spaced wall members, each with an upper end having an upper surface of predetermined contour;
    a service platform extending generally perpendicularly from the wall member and generally flush with the first end of the wall member, the service platform defining one or more recessed openings, each configured to receive a depth marker for application to an endodontic file;

a resiliently deformable cushion adapted for deformed seating within the socket-forming member, the cushion having an upper end with an upper surface which mimics, and is flush with, the upper surfaces of the upper ends of the wall members to collectively define a plurality of distinct, file-receiving regions in the cushion;

a medicament holder configured for selected securment to the socket-forming member, the holder having a generally U-shaped clip with an internal span which extends along an interior of the socket-forming member and an external span which extends along an exterior of the socket-forming member, the internal and external spans collectively securing the medicament holder to the socket-forming member, and with a cup which includes a generally conical interior well section and a generally cylindrical interior well section adjacent the generally conical interior well section;

a finger mount joined with a preselected wall member of the socket-forming member to provide for attachment of said system to a user's hand; and a measuring platform which extends from a preselected wall member above the finger mount, the measuring platform including a scale for use in setting a depth marker on an endodontic file.

* * * * *